United States Patent [19]

Gadd

[11] 4,063,104
[45] Dec. 13, 1977

[54] SCANNING X-RAY MACHINE ARRANGEMENT

[75] Inventor: Norman Arthur Gadd, Taplow, England

[73] Assignee: EMI Limited, Middlesex, England

[21] Appl. No.: 668,519

[22] Filed: Mar. 19, 1976

[30] Foreign Application Priority Data

Mar. 21, 1975   United Kingdom ............... 11850/75

[51] Int. Cl.² .......................... A61B 6/02; H01J 35/16
[52] U.S. Cl. ................................. 250/523; 250/445 T
[58] Field of Search ................... 250/422, 445 T, 419, 250/420, 523

[56] References Cited

U.S. PATENT DOCUMENTS

| | | | |
|---|---|---|---|
| 2,712,080 | 6/1955 | Koerner et al. ...................... | 250/523 |
| 3,037,119 | 5/1962 | Kizaur et al. ........................ | 250/523 |
| 3,541,334 | 11/1970 | Sobolewski .......................... | 250/523 |

*Primary Examiner*—Alfred E. Smith
*Assistant Examiner*—T. N. Grigsby
*Attorney, Agent, or Firm*—Cooper, Dunham, Clark, Griffin & Moran

[57] ABSTRACT

In a scanning X-ray machine involving at least rotational movement of a source about an axis, a flexible connection arrangement is provided for electricity, coolant and the like in which a connection handling arrangement includes a guide to form at least one guided loop between fixed and movable parts of the machine and inside the machine cover, the connection being taken in from and returned to the loop with said movement.

9 Claims, 3 Drawing Figures

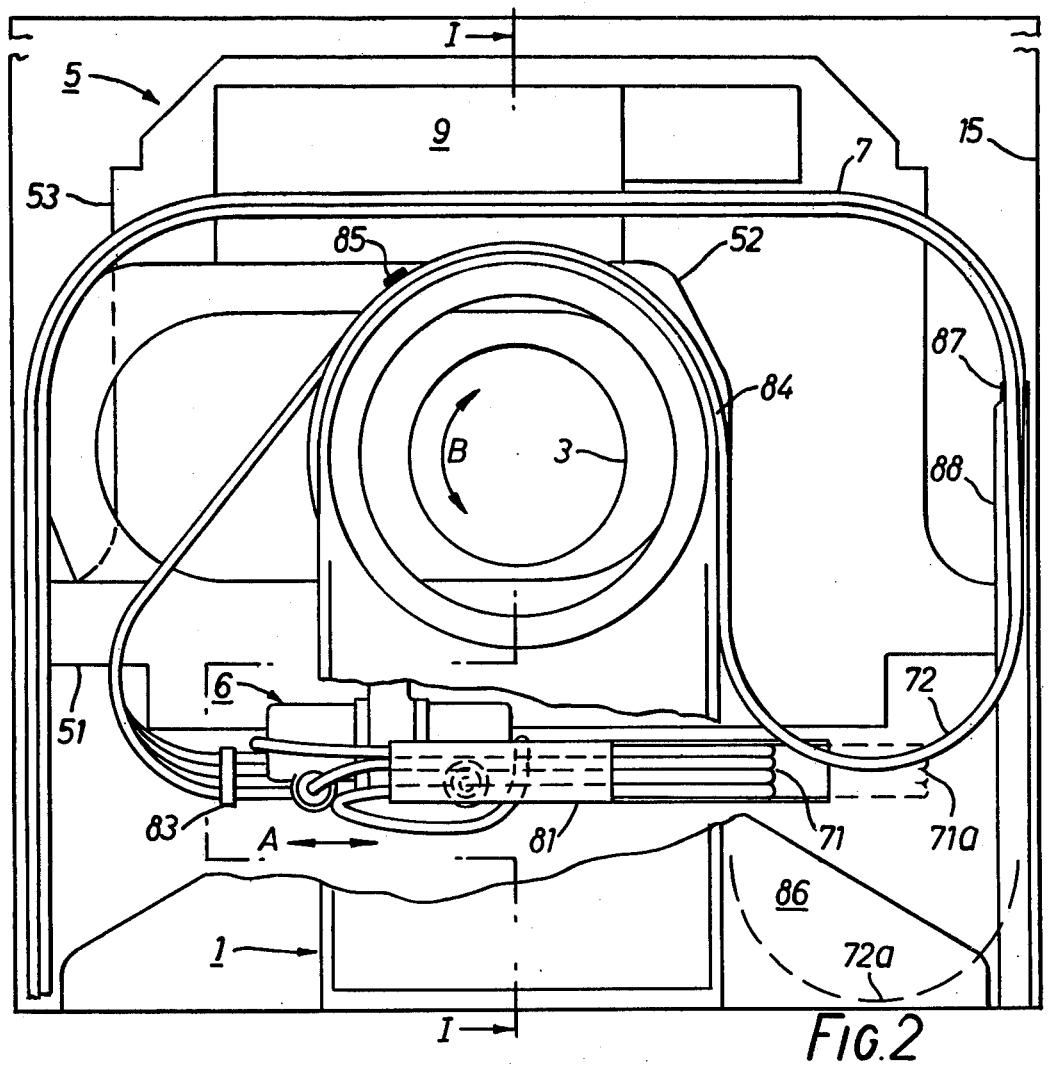
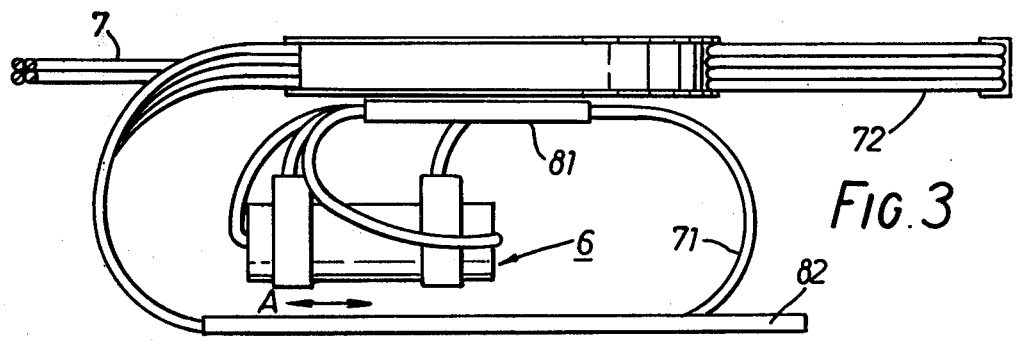

SCANNING X-RAY MACHINE ARRANGEMENT

This invention relates to flexible connections to rotatable and displacable apparatus such as an X-ray source in a scanning X-ray machine.

To permit apparatus such as an X-ray source to be rotated about an axis, or both rotated about an axis and displaced with respect to the axis, it is necessary to provide some slack in the flexible connections over which electric power and cooling fluid, such as oil, are supplied. The connections must be protected against undue flexing and too small a curvature. In arrangements proposed hitherto for linearly-moveable X-ray sources loops of connections are suspended around the machine, see for example Toshiba Review, July-August 1969, inside front cover and page 26. Such arrangements are not always successful in providing protection and also require a large amount of space around the apparatus which must be left clear for the connections to sweep through.

It is an object of the invention to provide an improved flexible connection arrangement.

According to the invention there is provided, in a scanning X-ray machine in which an X-ray source is supported inside a machine cover for scanning movement scanning to direct radiation along paths in various directions and has at least one flexible connection between movable and fixed machine parts, a connection handling arrangement including guide means to form at least one guided loop within the machine cover of each flexible connection, said guide means having a connection guide movable with the source and to which said connection is attached to take in and return said connection from and to said loop with movement of the source.

The X-ray source may be moved rotationally to direct radiation along paths inclined in different directions to an axis and the connection guide may be curved about said axis to vary the size of the loop with said movement.

The X-ray source may be moved along a line to direct radiation along various parallel directions and the connection guide may cause the loop to roll along the connection with said movement.

The curved guide may be between the loop of variable size and the rolling loop, the rolling loop extending to said source and being inclinable with said rotational movement of the source.

The curved guide may be a drum to which the connection is attached and about which drum the connection is wound.

The rolling loop may be formed to substantially the minimum bending radius of the connection between a straight fixed and a straight movable guide.

Embodiments of the invention will now be described with reference to the accompanying drawings in which:

FIGS. 2 and 3 show respectively a rear elevation and underside plan view of the machine of FIG. 1.

Figure 1:
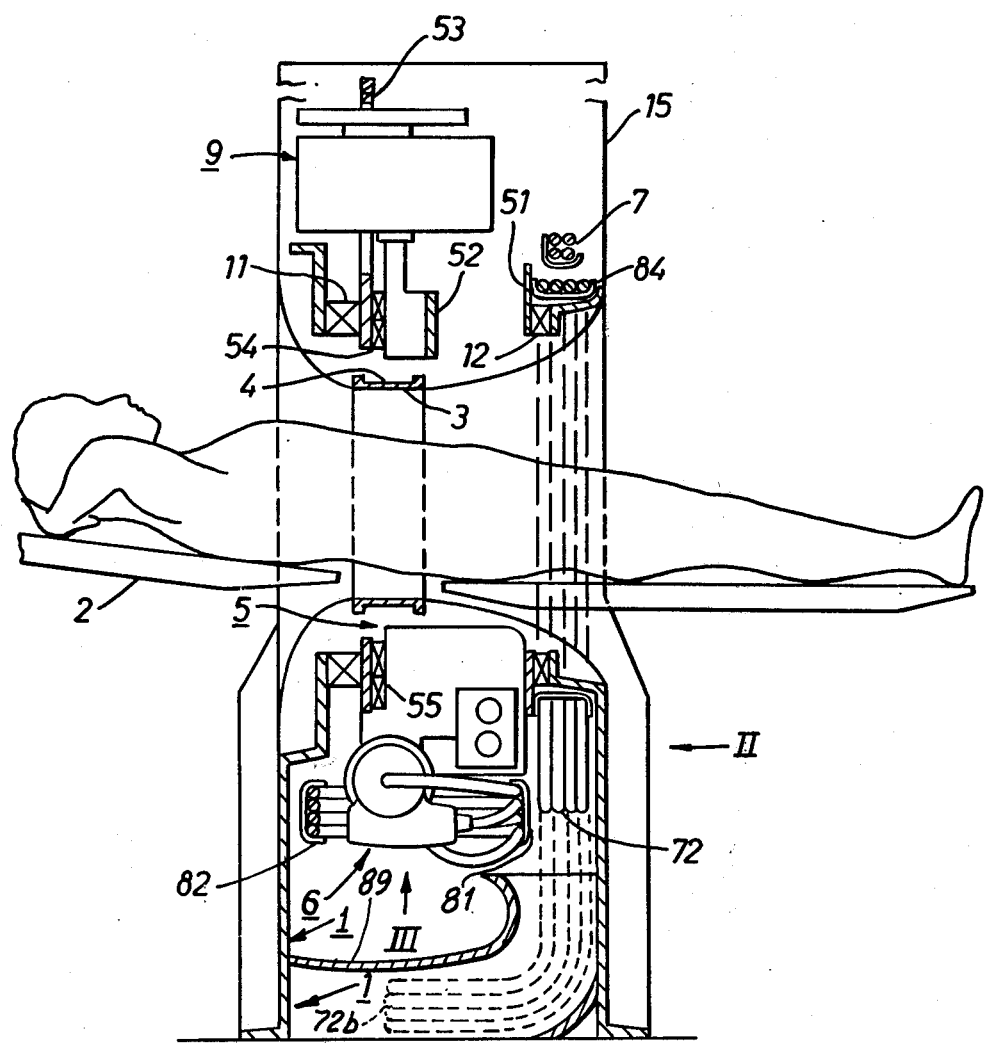
FIG. 1 shows a cross-sectional elevation of a scanning X-ray machine.

Considering all the figures of the drawings, the X-ray machine has a main frame 1 which may be placed on a flat floor surface of sufficient strength to support the machine without the provision of cable wells or the like. The frame 1 supports a two-part platform 2 (shown only in FIG. 1) on which a subject for examination is placed along an axis of the machine and retained, if required, in known manner with the part of the subject to be X-rayed in aperture 3. Aperture 3 is formed by a ring 4 of X-ray transparent material fixed to the main frame of the machine. The main frame also supports two bearings, 11 and 12, each in the vertical plane and extending around aperture 3.

The bearings 11 and 12 support a sub-frame 5 which is rotatable, through an angle which may be between 240° and 360°, around aperture 3. Sub-frame 5 is formed by a large, rectangular end plate 53 to which are attached another, smaller, end plate 51 and an intermediate yoke 52. The plates are joined by members, not shown, to form a rigid sub-frame supported on bearings 11 and 12 for rotation about the subject for examination. The sub-frame supports an X-ray source 6 and a detector unit 9. These items are linked by yoke 52 and move to and fro on bearings 54 and 55 extending along a path tangential to the circle of rotation about the subject. By use of the yoke the movements of the source and detector are kept in exact step, which is essential for the accuracy of the apparatus. A motor (not shown) drives the machine.

There is a balance weight (not shown) moved in opposition to the source to reduce vibration and bearing load due to the to and fro movement of the source. A balance weight (not shown) is also added to the detector 9 to balance the total of the source and its balance weight for rotational movement of the sub-frame.

The moving and fixed parts of the machine are enclosed in cover 15 which extends over the outside and through to the ring 4. The cover provides a smooth uncluttered outer surface which is of assistance in keeping the machine clean as well as improving its appearance. The manner of displacement is not shown as it is not essential to the invention and will be readily apparent to those skilled in the art. The construction described thus provides an arrangement by which an X-ray source can be rotated around an axis and displaced with respect to the axis to carry out a scanning examination of the subject.

The X-ray source requires both power and coolant supply connections and these must clearly be flexible to permit the movement of the source. Hitherto such connections have been provided with flexibility by attaching them to an articulated boom and providing slack at various bends to allow for the movement of the boom. Such arrangements can cause rapid wear of the connections, besides having a possibly untidy and unattractice appearance, particularly to a hospital patient.

The connections, reference 7, are typically four in number, two being liquid coolant flow and return flexible conduits and two being electrical flexible conductors. Each may be of a diameter of about one inch (25mm) and have a minimum bending radius of about one foot (300mm). The connections are relatively fragile and as they are flexed each time the machine is used care must be taken that they are not rapidly damaged by undue flexing, leading to failure of the machine. As the machine is both expensive and used for medical purposes such failure is both costly and can delay treatment of a patient.

Accordingly the invention provides a connection arrangement in which the guided loops are formed to permit movement of the subframe and the X-ray source respectively.

Consider firstly the X-ray source 6. The connections from the source are taken to a cable tray 81 and secured to the tray. The tray 81 is supported on sub-frame 5 so that it moves with the source and there is no flexing of the connections between the tray and the source. From the cable tray 81 the connections extend around a curve to another cable tray 82. Tray 82 is fixed to the sub-frame 5 and the connections are attached to the tray at one end by clamp 83. The rest of the connections may move freely between the trays when tray 81 moves with respect to tray 82. A rolling loop 71 of the connections is supported partly by the edges of the cable trays and partly by its own stiffness. As source 6 moves along the path indicated by arrow A the rolling of the loop transfers the connections from one tray to the other without excessive flexing. The loop moves from the position shown in solid line at 71 to the dotted outline 71a. As the source 6 moves with sub-frame 5 the connections between clamp 83 and source 6 need only flex to accommodate the displacement of source 6 with respect to sub-frame 5.

To allow for the rotation of sub-frame 5 the outer surface around aperture 3 is a curved guide in the form of a drum. To this end circular flange 51 of the sub-frame 5, supported by bearing 12, has a peripheral cable tray 84 to which the connections are clamped by clamp 85. As clamps 83 and 85 are both on sub-frame 5 and move together, the connection-run between the clamps is not subject to flexing and can be secured as required, allowing for the change of alignment of the connections from the vertical to the horizontal.

As sub-frame 5 rotates, as indicated by arrow B, connections will be reeled onto or off of the tray 84. To house the connections the main frame 1 includes a cable well 86. Connections from the tray 84 form a loop 72 in well 86 guided between tray 84 and tray 88 on the main frame and are secured to the main frame 1 by a clamp 87. Rotation of sub-frame 5 causes the loop 72 to move between the position shown in solid line and the dotted position 72a. The well 86 and loop 72 are sized so that the position 72a is above the base of the machine, thus avoiding the need for excavation in the floor supporting the machine. From clamp 87 the connections can be secured in any convenient way to the main frame 1 of the machine and connected to the machine as required.

It will be noted from FIGS. 1 and 2 that the loops 71 and 72 are arranged not to interfere with one another by including an axial displacement of the connections between clamps 83 and 85 on sub-frame 5.

The cable 86 shown in adequate for a 240° rotation of sub-frame 5, but for larger angles, even in excess of 360°, a larger well may be needed. To provide this cable tray 88 is made in the form of a quadrant of a cricle, centred on the axis about which the sub-frame 5 rotates and extending from below clamp 87 to vertically below the axis of sub-frame 5. This curved cable tray, together with the curved tray 84, forms an internal curved cable well extending forwardly from the plane of FIG. 1 and of constant breadth into which loop 72 can extend with rotation of sub-frame 5. The limit of this well across the machine, as seen in FIG. 2, is the region occupied by the four bunched cables entering the machine. If a still larger "well" is required, e.g. for rotations which may be in excess of 360° by two or three multiples, i.e. in the order of 1000°, the "well" can be extended perpendicular to the main frame of the machine, i.e. transversely of the view in FIG. 1. The loop 72 can be guided by cable trays to spread sideways, to the left and right in FIG. 1. One such cable tray is indicated at 89 in FIG. 1 and the loop at 72b. In a typical machine for examining a human body cable tray 84 has a radius of curvature of about 20 inches (0.5m) and thus one complete revolution uses about 10 feet (3m) of connection. By employing the perpendicularly extending "well" the connections required for at least two complete revolutions of tray 84, and thus the X-ray source and detectors, can be accommodated in a "well" of substantially the same extent as the patient support 2 and thus not increase the area required for the machine. If required the connections in tray 84 may be bunched as are connections 7 to reduce the width of the tray and thus the movable part of the machine.

What I claim is:

1. In a scanning X-ray machine in which an X-ray source is supported inside a machine cover for scanning movement to direct radiation along substantially coplanar paths in various directions and has at least one flexible connection between movable and fixed machine parts, a connection handling arrangement including guide means to form at least one guided loop extending unsupported within the machine cover of each flexible connection, said guide means having a connection guide which is movable with the source and to which said connection is attached to take in and return said connection from and to said loop with movement of the source.

2. A machine according to claim 1 including means for orbiting the X-ray source to direct radiation along paths inclined in different directions with respect to each other but being at about the same angle to an axis and wherein the connection guide is curved about said axis to vary the size of the loop with said movement and to thereby form a loop of variable size.

3. A machine according to claim 2 including means for moving the X-ray source along lines transverse to said axis to direct radiation along directions which are substantially parallel to each other for each line and wherein the connection guide causes the loop to roll along the connection with said movement and forms thereby a rolling loop.

4. A machine according to claim 3 in which the curved guide is between the loop of variable size and the rolling loop, the rolling loop extending to said source and being inclinable with said orbiting movement of the source.

5. A machine according to claim 2 in which the curved guide comprises a drum to which the connection is attached and about which drum the connection is wound.

6. A machine according to claim 3 in which the rolling loop is formed to substantially the minimum bending radius of the connection between a straight fixed and a straight movable guide.

7. A machine according to claim 2 including a floor engaging machine frame, wherein the source and curved guide are orbited through at least 270° about a horizontal axis and the variable loop is guided in a vertical plane within the floor engaging frame of the machine.

8. A machine according to claim 7 in which the loop is guided for movement in a curved path in the vertical plane.

9. A machine according to claim 5 including a floor engaging machine frame, wherein the source and drum are orbited through at least 360° about a horizontal axis and the loop is guided in a vertical plane in a curved path within the floor engaging frame of the machine and is further guided in the horizontal plane within the floor engaging frame.

* * * * *